United States Patent [19]
Wright et al.

[11] Patent Number: 5,842,476
[45] Date of Patent: Dec. 1, 1998

[54] METHOD FOR CONTROLLING FERTILITY

[75] Inventors: Jeri Dawn Wright, Dublin; Jerry D. Childers, Fremont; Brian L. Barclay, Sunnyvale; Patrick S.-L. Wong, Palo Alto; Linda E. Atkinson, Portola Valley, all of Calif.

[73] Assignee: ALZA Corporation, Palo Alto, Calif.

[21] Appl. No.: 437,758

[22] Filed: May 9, 1995

Related U.S. Application Data

[63] Continuation of Ser. No. 37,056, Mar. 25, 1993, and Ser. No. 805,241, Dec. 9, 1991, Pat. No. 5,200,197, which is a division of Ser. No. 437,480, Nov. 16, 1989, Pat. No. 5,098,714.

[51] Int. Cl.⁶ ............................. A61B 19/00; A61K 9/24
[52] U.S. Cl. ...................... 128/898; 604/891.1; 424/473; 424/474
[58] Field of Search ............................. 604/890.1–892.1; 424/473, 468, 474; 514/170; 128/898

[56] References Cited

U.S. PATENT DOCUMENTS

| | | | |
|---|---|---|---|
| 1,881,197 | 12/1932 | Kirk | 424/471 |
| 2,799,241 | 7/1957 | Wurster | 118/24 |
| 3,133,132 | 5/1964 | Loeb et al. | 264/49 |
| 3,284,302 | 11/1966 | Kinci | 424/471 |
| 3,313,701 | 4/1967 | Babcock | 424/472 |
| 3,845,770 | 11/1974 | Theeuwes et al. | 128/130 |
| 3,916,899 | 11/1975 | Theeuwes et al. | 128/260 |
| 4,063,064 | 12/1977 | Saunders et al. | 219/121 |
| 4,088,864 | 5/1978 | Theeuwes et al. | 219/260 |
| 4,160,020 | 7/1979 | Ayer et al. | 424/15 |
| 4,177,256 | 12/1979 | Michaels et al. | 424/22 |
| 4,200,098 | 4/1980 | Ayer et al. | 128/260 |
| 4,285,987 | 8/1981 | Ayer et al. | 427/3 |
| 4,309,996 | 1/1982 | Theeuwes | 128/260 |
| 4,320,759 | 3/1982 | Theeuwes | 128/260 |
| 4,449,983 | 5/1984 | Cortese et al. | 604/892 |
| 4,576,604 | 3/1986 | Guittard et al. | 604/892.1 |
| 4,629,449 | 12/1986 | Wong | 604/890.1 |
| 4,673,405 | 6/1987 | Guittard et al. | 424/473 |
| 4,772,474 | 9/1988 | Eckenhoff et al. | 424/465 |
| 4,810,502 | 3/1989 | Ayer et al. | 424/473 |
| 4,814,182 | 3/1989 | Graham et al. | 424/484 |
| 4,842,867 | 6/1989 | Ayer et al. | 424/471 |
| 4,948,592 | 8/1990 | Ayer et al. | 424/471 |
| 4,948,593 | 8/1990 | Wright et al. | 424/473 |
| 4,962,098 | 10/1990 | Boissonneault | 514/170 |
| 4,986,987 | 1/1991 | Ayer et al. | 424/471 |
| 5,019,397 | 5/1991 | Wong et al. | 424/473 |
| 5,023,076 | 6/1991 | Ayer et al. | 424/473 |
| 5,032,406 | 7/1991 | Dansereau et al. | 424/472 |
| 5,098,714 | 3/1992 | Wright et al. | 424/473 |

FOREIGN PATENT DOCUMENTS

| | | | |
|---|---|---|---|
| 2166051 | 4/1986 | United Kingdom | 604/890.1 |

OTHER PUBLICATIONS

Wurster, Dale E., J. Am. Pharm. Assn., Sci. Ed., vol. 49 (1960) pp. 82–84.

Wurster, Dale E., J. Am. Pharm. Assn., Sci. Ed., vol. 48 (1959) pp. 451–454.

The Pharmacological Basis of Therapeutics, Goodman & Gilman, 7th Ed. (1985) pp. 1430–1439.

Pharmaceutical Sciences, Remington, 14th Ed. (1970) pp. 1626–1680.

*Primary Examiner*—Robert A. Clarke
*Attorney, Agent, or Firm*—Paul L. Sabatine; Pauline A. Clarke; Christopher P. Rodgers

[57] ABSTRACT

An osmotic device is disclosed comprising an exterior coat comprising an estrogenic and a progestogenic steroid that are delivered immediately as a contraceptive pair for fertility regulation in a female, and a compartment comprising an estrogenic steroid that is delivered at a controlled rate over a prolonged period of time for fertility regulation in a female.

2 Claims, 2 Drawing Sheets

METHOD FOR CONTROLLING FERTILITY

CROSS-REFERENCE TO RELATED APPLICATIONS

This application is a continuation of application Ser. No. 08/037,056, filed Mar. 25, 1993, and benefit of the filing date of said earlier filed application is claimed under 35 U.S.C. §120, and a continuation of U.S. Ser. No. 07/805,241, filed on Dec. 9, 1991, now U.S. Pat. No. 5,200,197, which application Ser. No. 07/805,241 is a division of U.S. Ser. No. 07/437,480 filed on Nov. 16, 1989, and issued as U.S. Pat. No. 5,098,714 on Mar. 24, 1992, which applications are incorporated herein by reference, and benefit is claimed of their filing date. These applications are assigned to the ALZA Corporation of Palo Alto, Calif.

DESCRIPTION OF TECHNICAL FIELD

This invention pertains to an osmotic oral dosage form useful for fertility control. The dosage form provides an initial pulsed delivery of a progestogen and an estrogen followed by a prolonged delivery of an estrogen. The invention concerns also a method of administering orally the dosage form for providing a pulsed delivery of a progestogen and an estrogen followed by the controlled delivery of an estrogen over an extended period of time.

DISCLOSURE OF BACKGROUND OF THE INVENTION

A continuous need exists for fertility control for providing freedom for women to choose when they want to have children. Efforts were made, in the early 1960's, to satisfy the need for fertility control with the introduction of the oral contraceptive pill comprising an estrogenic steroid and a progestational steroid. The contraceptive pill used by the prior art comprises a tablet form that delivers the steroids in a bulk, nonrate, uncontrolled dose. In one prior art contraceptive regimen, a tablet comprising both an estrogen and a progestin are administered for about three weeks, while in another modification a tablet comprising an estrogen is administered for about two weeks and a tablet comprising an estrogen and progestin are administered for about a week. The contraceptive steroids were delivered as an oral tablet devoid of rate-controlled delivery properties because the contraceptive steroids are practically insoluble in aqueous fluids and, accordingly, they do not lend themselves for manufacture into a dosage form that administers the steroids at a controlled and known rate per unit time.

The contraceptive steroids, moreover, were delivered by the prior art in a dose unprotected from the changing environment of the gastrointestinal tract, with little consideration for the steroid's pharmacological and physiological effects and the accompanying disadvantages on a recipient. For example, one disadvantage associated with the prior art tablet accompanies the dose-dumping of estrogen which can lead to gastrointestinal disturbances, nausea, weight-gain, edema, and an increase in the incidence of thrombophelibitis and associated cardiovascular disorders. Also, the prior art tablet does not provide for the fast release of a progestational steroid for avoiding liver metabolism of the steroid and the subsequent delivery of an estrogen in small continuous doses for lessening the incidence of side effects in the recipient. The oral contraceptives are disclosed in *The Pharmacological Basis of Therapeutics*, by Goodman and Gilman, 7th Ed., pages 1430 to 1439 (1985), published by Macmillian Publishing Company.

DISCLOSURE OF OBJECTS OF THE INVENTION

Accordingly, in view of the above presentation, it is an immediate object of this invention to provide a dosage form comprising an estrogen and a progestogen that can be administered for fertility control, and which dosage form substantially overcomes the disadvantages and omissions associated with the prior art.

Another object of the present invention is to provide a dosage form for co-administering an estrogen and a progestogen in a pulsed dose followed by the rate-controlled delivery of an estrogen over a prolonged period of time for fertility control in a warm-blooded female.

Another object of the invention is to provide a pharmaceutically acceptable dosage form manufactured as an osmotic dosage form that makes available initially an estrogen and a progestogen followed by sustained and controlled delivery of an estrogen.

Another object of the invention is to provide a novel dosage form manufactured as an osmotic device that can administer the steroids estrogen and progestogen immediately on entering the gastrointestinal tract for passage to a biological receptor site to produce the desired contraceptive effect, followed by administering estrogen only to the biological receptor site for the intended effect.

Another object of the invention is to provide an osmotic dosage form that comprises two regimens of steroid administration in the same dosage form, comprising (1) a first regimen that administers a steroid pair comprising an estrogen and a progestogen and (2) a second regimen that administers an estrogen, and wherein the osmotic dosage form substantially eliminates the unwanted influences of the gastrointestinal environment on the steroids while they reside in the dosage form, and also provides for instant administration of the steroid by the first regimen and the controlled, low-dose administration or the steroid during the second regimen.

Another object of the invention is to provide an osmotic dosage form that can deliver a progestational steroid at a pulsed rate of delivery for substantially lessening liver metabolism of the steroid.

Another object of the invention is to provide an osmotic dosage form that can deliver an estrogen steroid in small amounts for substantially lessening the incidence of side effects.

Another object of the present invention is to provide an osmotic dosage form that can deliver a substantially aqueous insoluble estrogen and progestogen pair at a pulsed rate, and then deliver an aqueous insoluble estrogen at a controlled and continuous rate over time.

Another object of the present invention is to provide an osmotic dosage form adapted for oral administration of an estrogen and a progestogen, which dosage form comprises an external pulse released coat comprising an estrogen and a progestogen, and a compartment comprising a first composition comprising an estrogen and a contacting second expandable composition, which compositions operate together for the controlled administration of an estrogen over time.

Another object of the present invention is to provide a complete oral contraceptive regimen useful for women of childbearing age which regimen comprises an osmotic dosage form and a method of contraception, the use of which osmotic dosage form and method of contraception requires intervention only for initiation of the contraceptive regimen.

Another object of the invention is to provide a composition of matter comprising an estrogen, a progestogen and a cellulose polymer, which composition can be externally stored on and dispensed from an osmotic device for the purpose of fertility control.

Another object of the invention is to provide a method for producing contraception by orally administering an estrogen and a progestogen to a warm-blooded animal desiring fertility control.

Another object of the invention is to provide a contraceptive regimen comprising eighteen to twenty-three dosage forms, which dosage forms deliver a pulsed dose of a progestational and estrogenic steroid followed by a continuous dose of an estrogenic steroid.

Other objects, features, and advantages of the invention will be more apparent to those skilled in the dispensing arts from the following detailed specification, taken in conjunction with the drawing figures and the accompanying claims.

BRIEF DISCLOSURE OF THE DRAWINGS

In the drawing figures, which are not drawn to scale but are set-forth to illustrate various embodiments of the invention, the drawing figures are as follows:

Drawing

Drawing FIG. 2 is an opened view of the dosage form of drawing FIG. 1 through 2—2, wherein drawing FIG. 2 depicts the wall of the dosage form carrying on its exterior surface an aqueous-fluid releasable coat comprising an estrogen and a progestogen pair, or a progestogen, with the compartment of the dosage form comprising an estrogen;

Drawing FIG. 3 is an opened view of the dosage form of drawing FIG. 1 through 2—2 wherein drawing FIG. 3 depicts another embodiment comprising a pair of steroids releasably carried in the wall of the dosage form;

Drawing

Drawing

In the drawings and in the specification, like parts in related drawing figures are identified by like numbers. The terms appearing earlier in the specification and in the description of the drawing figures, as well as embodiments thereof, are further detailed elsewhere in the disclosure.

DETAILED DISCLOSURE OF THE DRAWING FIGURES

Figure 1:
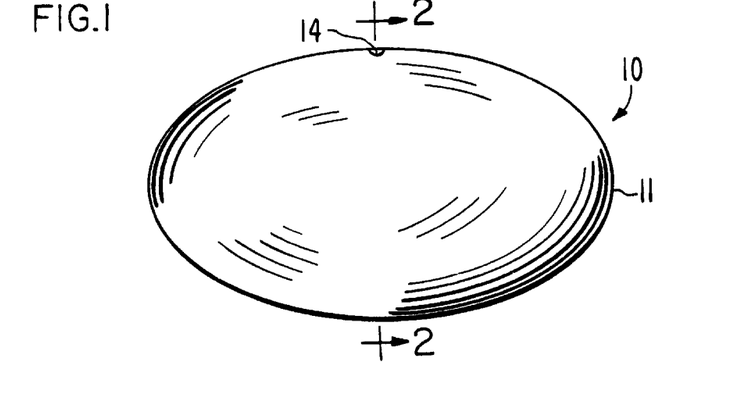
FIG. 1 is a view of a single surface of a dosage form adapted and shaped for orally administering a contraceptive pair of steroids followed by administering a single steroid to the gastrointestinal tract of a warm-blooded female.

Turning now to the drawing figures in detail, which drawing figures are examples of the dosage form provided by this invention, and which examples are not to be construed as limiting the invention, one example of the dosage form is illustrated in drawing FIG. 1 and designed by the numeral 10. In drawing FIG. 1, dosage form 10 comprises a body 11 sized, shaped and adapted for oral administration into the gastrointestinal tract of a human. Dosage form 10 comprises at least one orifice 14 that connects the inside with the outside of dosage form 10.

Figure 2:
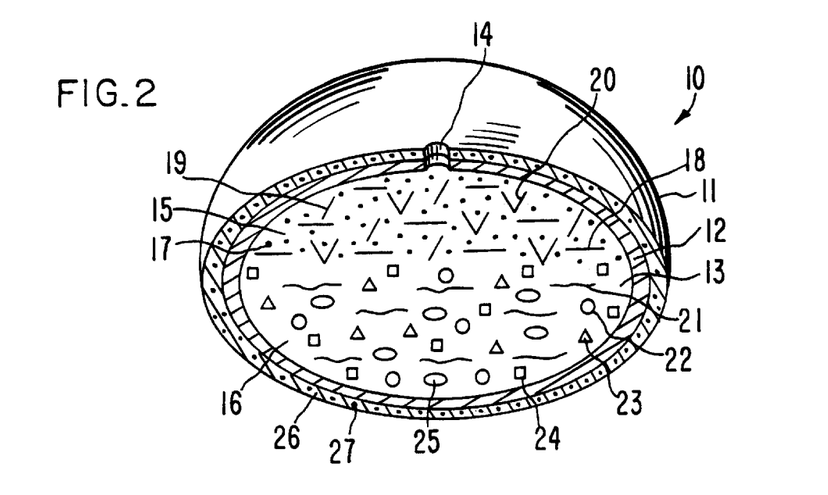

In drawing FIG. 2, dosage form 10 is seen in opened view through 2—2 of drawing FIG. 1. In drawing FIG. 2, dosage form 10 is manufactured as an osmotic device. The osmotic dosage form 10 comprises a body 11, a wall 12, which surrounds and defines an internal compartment 13. Wall 12 comprises at least one exit means 14 that connects internal compartment 13 with the exterior of dosage form 10. Dosage form 10 can comprise more than one exit means 14. Wall 12 of dosage form 10 comprises in at least a part a semipermeable composition that is permeable to the passage of an exterior fluid present in the environment of use. The composition comprising wall 12 is substantially inert, and it maintains its physical and chemical integrity during the dispensing life of contraceptive steroids from osmotic dosage form 10. The phrase, "keeps its physical and chemical integrity," means wall 12 does not lose its structure and it does not change chemically during the contraceptive dispensing life of dosage form 10.

Wall 12, in a presently preferred embodiment, comprises a cellulosic polymer composition. The cellulosic polymer comprises a member selected from the group consisting of a cellulose ester, cellulose ether, cellulose ester-ether, cellulose acylate, cellulose diacylate, cellulose triacylate, cellulose acetate, cellulose diacetate and cellulose triacetate. The cellulosic polymers comprise a degree of substitution, D.S., on the anhydroglucose unit from greater than 0 up to 3, inclusive. By degree of substitution is meant the average number of hydroxyl groups originally present on the anhydroglucose unit comprising the cellulose polymer that are replaced by a substituting group. Exemplary polymers comprise cellulose acetate having a D.S. up to 1 and an acetyl content up to 21%; cellulose acetate having an acetyl content of 32% to 39.8%; cellulose diacetate having a D.S. of 1 to 2 and an acetyl content of 21% to 35%; cellulose triacetate having a D.S. of 2 to 3 and an acetyl content of 35% to 44.8%, and the like. Other examples comprise cellulose propionate having a D.S. of 1.8, a propanol content of 39.2% to 45% and a hydroxyl content of 2.8% to 5.4%; cellulose acetate butyrate having a D.S. of 1.8, an acetyl content of 13% to 15% and a butyryl content of 34% to 39%; cellulose acetate butyrate having an acetyl content of 2% to 29%, a butyryl content of 17% to 53% and a hydroxyl content of 0.5% to 4.7%; cellulose triacylates having a D.S. of 2.9 to 3 such as cellulose trivalerate, cellulose trilaurate, cellulose tripalmitate, cellulose trisuccinate, and cellulose trioctanoate; cellulose diacylates having a D.S. of 2.2 to 2.6 such as cellulose disuccinate, cellulose dipalmitate, cellulose dioctanoate, cellulose dipentale, and the like. Additional cellulose polymers that may be present in wall 12 comprise ethyl cellulose comprising an ethoxy group degree of substitution of 1.5 to 3, about 40% to 50% ethoxy content, and a viscosity range of 7 to 100 centipoises, or higher; a cellulose ether selected from the group consisting of hydroxypropylcellulose, hydroxypropylmethylcellulose and hydroxyethylcellulose, and the like. In one preferred manufacture wall 12 comprises 100 weight percent (wt %) of a cellulosic polymer as disclosed above; in another preferred manufacture wall 12 comprises from 60 weight percent to 90 weight percent of a member selected from the group consisting of a cellulose acylate, cellulose diacylate and cellulose triacylate polymer, from 15 to 45 weight percent of an ethyl cellulose and from 0 to 25 weight percent of a polyethylene glycol with the total amount of all wall-components comprising wall 12 equal to 100 weight percent; and another embodiment comprising 45 to 80 weight percent of a member selected from the group consisting of a cellulose acylate, cellulose diacylate and cellulose triacylate, from 15 to 45 weight percent of an ethyl cellulose, from 0.5 to 25 weight percent of a cellulose ether selected from the group consisting of hydroxypropylcellulose, hydroxyethylcellulose, and hydroxypropylmethylcellulose, and from 0 weight percent to 30 weight percent of polyethylene glycol, with the total amount of all components comprising wall 12 equal to 100 weight percent. The cellulosic polymers are known in U.S. Pat. Nos. 3,133,132; 3,845,770; 3,916,899 and 4,160,000; and in the *Handbook of Common Polymers* by Scott, J. R. and Roff W. J., (1971) published by CRC Press Cleveland, Ohio.

Internal compartment 13 comprises a first-compositional layer 15 and a second-compositional layer 16. The first layer 15 can be defined optionally as a first composition 15, and the second layer 16 also can be defined optionally as a second composition 16. The first layer 15 and the second layer 16 initially are in laminar arrangement and they cooperate with each other and with dosage form 10 for delivering contraceptively effective dose amounts of a contraceptive estrogen from compartment 13 of dosage form 10.

The contraceptive estrogen steroids possessing estrogenic activity present in first layer 15 that can be dispensed from compartment by dosage form 10 to a warm-blooded female recipient comprise estrogen steroids 17 represented by cots. The estrogen active steroids comprise a member selected from the group consisting of estradiol, estradiol valerate, estradiol benzoate, estradiol cypionate, estradiol propionate, estradiol dipropionate, estradiol acetate, ethinyl estradiol, 17α-ethinyl estradiol esters, 17α-ethinyl estradiol acetate, 17α-ethinyl estradiol benzoate, 17α-ethinyl estradiol ethers, estrone, estrone acetate, estrone sulfate, estriol, estriol succinate and estriol triacetate. Generally, compartment 13 comprises about 0.005 milligrams to 0.750 milligrams of an estrogenically-active, fertility-regulating pharmaceutically acceptable steroid, which estrogenic steroid is delivered in small amounts from 0.2 micrograms to 30 micrograms per hour for 8 to 24 hours and usually for 12 to 24 hours.

Estrogenic steroid 17 present in compartment 13 is present in a composition, wherein estrogenic steroid 17 is blended with a pharmaceutically acceptable carrier, which carrier comprises from 20 mg to 300 mg of a polyethylene oxide comprising a 50,000 to 350,000 horizontal molecular weight and identified as horizontal dashes 18, and from 0.05 mg to 75 mg of a polyvinyl pyrrolidone comprising a 8,000 to 65,000 molecular weight as identified by slanted dashes 19, and from 0 to 8 mg of a lubricant identified by the letter V with the accompanying number 20 such as magnesium stearate, calcium stearate, stearic acid or the like.

Second layer 16 comprises, in a presently preferred embodiment, comprises 20 mg to 300 mg of a polyethylene oxide comprising a 4,000,000 to 7,500,000 molecular weight as identified by wavy lines 21, from 1 mg to 50 mg of a osmotically active compound such as a member selected from the group consisting of sodium chloride, potassium chloride, and the like, as identified by circles 22, from 0.05 mg to 35 mg of a hydroxypropylmethylcellulose exhibiting a molecular weight of 9,200 to 30,000 and identified by triangles 23, from 0 mg to 100 mg of an acrylic carboxyl polymer comprising a molecular weight of 1,250,000 to 4,000,000 and identified by squares 24, and from 0 mg 7.5 mg of a lubricant such as magnesium stearate, calcium stearate, stearic acid, and the like, as identified by oval 25. Second layer 16 optionally comprises from 0.10 mg to 5 mg of ferric oxide and optionally from 0.001 mg to 3 mg of FD & C blue lake #1.

Dosage form 10, as seen in drawing FIG. 2, comprises an exterior coat. Coat 26 is on the exterior surface of semipermeable wall 12. Coat 26 comprises a composition represented by dots 27, which composition 27 comprises an estrogenic steroid and a progestational steroid pair. Composition 27 also comprises a pharmaceutically acceptable steroid carrier selected from the group consisting of a hydroxypropylmethylcellulose, a hydroxypropylethylcellulose, a hydroxypropylcellulose or a hydroxyethylmethylcellulose and, optionally, a polyethylene glycol, or an optional polyvinyl pyrrolidone, for providing instantly the release of the contraceptive steroid pair from coat 26 to a female receptor. Coat 26, in operation in the gastrointestinal tract, dissolves or undergoes dissolution and concurrently therewith delivers the steroids. Coat 26 comprises at least one of the estrogenic steroids disclosed earlier in this specification. Coat 26 by immediately delivering an estrogenic steroids provides immediate fertility control, and thereby essentially overcomes the time required by dosage form 10 to deliver an estrogenic steroid from compartment 15. Dosage form 10 needs a start-up time for imbibing an exterior fluid through wall 12 into compartment 15 to activate second layer 16 causing it to expand, push and displace the first layer through port 14.

Coat 26 comprises at least one progestational steroid that is released as a single dose for lessening metabolism by the liver. Contraceptive steroids possessing progestational activity present in coat 26 comprise a member selected from the group consisting of progesterone, d-norgestrel, norethindrone, levonorgestrel, norgestimate, norethisterone, norethisterone acetate, norethynodrel, norethindrone acetate, 17-hydroxyprogesterone, 17-hydroxyprogesterone esters, 19-nor-17-hydroxyprogesterone, 19-nor-17-hydroxyprogesterone esters, 17α-ethinyl-testosterone, 17α-ethinyl-19-nortestosterone, D-17β-acetoxy-13β-ethyl-17α-ethinyl-gon-4-en-3-one oxime, d-13β-ethyl-17α-ethinyl-17β-hydroxygon-4-en-3-one, 13β-ethyl-17β-hydroxygon-4-en- 3-one, 13β,17α-diethyl-17β-hydroxygon-4-en-3 one, ethylnodiol diacetate, medroxyprogesterone, chlormadione acetate, dimethistrone, 17α-ethinyl-17β-acetoxy-19-norandrost-4-en-3-one oxime, 3-keto-desogestrel, desogestrel, gestodene, gestodene acetate, medroxyprogesterone acetate and megestrol, medroxyprogesterone acetate and megestrol acetate, ethinyl estrodiol and gestodene, ethinyl estrodiol and desogestrel, and the like.

Coat 26 provides immediate delivery of the contraceptive steroid pair for quicker plasma steroid levels. Coat 26 generally comprises 10 nanogram to 25 milligrams of an estrogen and from 15 nanograms to 150 mg of a progestational steroid. Representative steroid pairs present in coat 26 are exemplified by ethinyl estradiol and norethindrone, ethinyl estradiol and norgestrel, ethinyl estradiol and norethisterone, ethinyl estradiol and levonorgestrel, ethinyl estradiol and norgestimate, estradiol valerate and levonorgestrel, estrone and norethindrone, estradiol propionate and ethinyl-19-nortestosterone, estriol and acetoxy-13β-ethyl-17α-ethinyl-17β-hydroxygon-4-en-3-one oxime, estriol and D-13β-ethyl-17α-ethinyl-17β-hydroxygon-4-en-3-one, estriol succinate and 3-keto-desogestrel, estrone sulfate and desogestrel, estradiol cypionate and gestodene, estradiol benzoate and medroxyprogesterone acetate, estradiol dipropionate and megestrol acetate, and the like. Coat 26 also comprises from 0.15 mg to 100 mg of a member selected from the group consisting of hydroxypropylmethylcellulose, hydroxypropylethylcellulose, hydroxypropylcellulose and hydroxyethylmethylcellulose wherein the cellulose member comprises a 9,000 to 50,000 molecular weight, from 0 to 50 mg of a polyethylene glycol and from 0 to 75 mg of a polyvinylpyrrolidone comprising a 8,500 to 45,000 molecular weight. Coat 26, in operation in gastrointestinal fluid, begins to release contraceptive steroid instantly, that is, when the fluid contacts coat 26. Coat 26 instantly releases the steroid pair in from zero to 60 minutes, usually from zero to 30 minutes, for immediate passage of the steroid pair into the systemic circulation of a recipient. Delivery system 10 is another embodiment optionally comprises a color overcoat of 0.01 to 10 mg of a commercially available blue colorant. Also, delivery system 10 can alternately be encompassed with an outer taste-mask preferably consisting of 0 to 10 mg of a hydroxypropylmethylcellulose.

Coat 26 unexpectedly comprises and delivers both an estrogenic and a progestogenic steroid in a deliverable composition for their concomitant contraceptive effect. It is unexpected and unforeseen that an estrogenic steroid and a different progestogenic steroid can be coated together and delivered simultaneously in a contraceptive dose amount. This is so as estrogenic and the progestogenic steroids each possess different coating properties, different dispensing kinetics, different physical properties, different molecular structure substituents, different solubilities, and different concentrations in the coat. The estrogenic and the progestogenic steroids are present in the exterior coat substantially-free of interaction, and they are available for immediate use for their simultaneous contraceptive effect.

Figure 3:
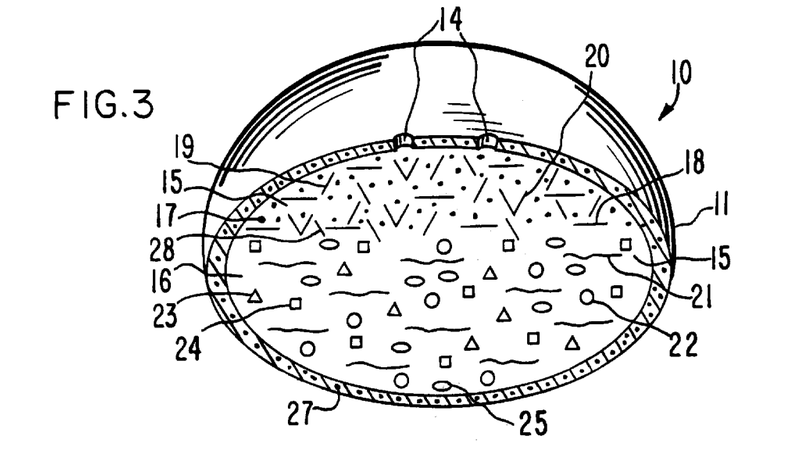

Drawing FIG. 3 depicts another embodiment provided by the invention. In drawing FIG. 3, dosage form 10 is seen in opened section, and it comprises a wall 12 that surrounds internal compartment 13, with at least one exit means 14 through wall 12. Internal compartment 13 comprises layer 15 comprising an estrogenic steroid 17, a polyethylene oxide 18, an optional polyvinylpyrrolidone 19, an optional antioxidant, 28, such as butylated hydroxy toluene or butylated hydroxyanisole, and a lubricant 20. Internal compartment 13 also comprises a second layer 16, which layer 16 comprises a polyethylene oxide 21, an osmagent 22, a hydroxypropylmethylcellulose 23, an optional acrylic carboxyl polymer 24, and a lubricant 25. Wall 12 in dosage form 10 in this embodiment comprises steroid composition 27, which steroid composition is leached by fluid of the gastrointestinal tract from wall 12 in zero to 60 minutes.

The expression, "exit means 14," as used herein, comprises means and methods suitable for the controlled metered release of estrogenic steroid from compartment 13 of dosage form 10. Exit means 14 is sized and adapted for the metered release of estrogenic steroid from dosage form 10. Exit means 14 includes at least one passageway, orifice, or the like, through wall 12 for communicating with the contraceptive steroids dosage in compartment 13 of dosage form 10. The expression, "at least one passageway," includes aperture, orifice, bore, pore, porous element, and the like, through which the contraceptive steroids can migrate, a hollow fiber, capillary tube, porous overlay, porous insert, composite semipermeable contacting microporous insert, or the like. The expression includes also a material that erodes or is a material that is leached from wall 12 in a fluid environment of use to produce at least one passageway in wall 12. Representative materials suitable for forming at least one passageway, or a multiplicity of passageways, include an erodible polyglycolic acid, or a polylactic acid member in wall 12, a gelatinous filament, polyvinyl, alcohol, a leachable material such as a fluid removable pore forming polysaccharide, polyol, salts, oxide, or the like. A passageway, or a plurality of passageways can be formed by leaching a material such as sorbitol, fructose, maltose, lactose, or the like, from wall 12. The passageway 14 can have any shape such as round, triangular, square, elliptical, and the like, for assisting in the metered release of the contraceptive steroids from dosage form 10. Dosage form 10 can be constructed with one or more passageway in spaced apart relation, or more than one passageway on a single surface of dosage form 10. Passageways and equipment for forming passageways are disclosed in U.S. Pat. Nos. 3,845,770 issued November 1974 to Theeuwes et al; 4,068,064 issued December 1977 to Saunders et al; and 4,088,864 issued May 1978 to Theeuwes et al. Passageways in osmotic systems formed by leaching are disclosed in U.S. Pat. Nos. 4,200,098 issued April 1980 to Ayer et al; 4,285,987 issued August 1981 to Ayer et al; 4,309,996 issued January 1982 to Theeuwes; and 4,320,759 issued March 1982 to Theeuwes.

Dosage form 10 of the present invention is manufactured by standard techniques. For example, in one embodiment a beneficial contraceptive estrogenic steroid is mixed with the pharmaceutically acceptable osmopolymer that acts as a carrier for the contraceptive estrogenic steroid, and with other composition forming ingredients and then pressed into a solid layer possessing dimensions that correspond to the internal dimensions of the compartment space adjacent to the passageway. In another manufacture, the beneficial estrogenic contraceptive steroid and other composition forming ingredients and a non-toxic solvent are mixed into a solid or a semisolid state, by conventional methods such as ballmilling, calendering, stirring or rollmilling, and then pressed into a preselected layer forming shape. Next, a layer of a composition comprising an osmopolymer and an optional osmagent are placed in contact with the layer comprising the beneficial estrogenic contraceptive steroid, and the two layers comprising the compartment are surrounded with a semipermeable wall. The layering of the first beneficial controlling estrogenic steroid composition and the second osmopolymer composition can be accomplished by using a two-layer tablet press. The wall can be applied by molding, spraying or dipping the pressed shapes into wall forming compositions. Another preferred technique that can be used for applying wall 12 is the air suspension coating procedure. This procedure comprises suspending and tumbling the two layered compositions in a current of air until the wall-forming composition surrounds the layers. The exterior instant release coat comprising the contraceptive steroid also can be formed by using the air suspension technique. The air suspension procedure is well suited for independently forming a wall or an exterior quick-release coat. The air suspension procedure is described in U.S. Pat. No. 2,799,241; in *J. Am. Pharm. Assoc.,* Vol. 48, pp 451–59. (1959); and ibid. Vol. 49, pp 82–84. (1960). Dosage forming systems 10 also can be coated with the wall-forming compositions with a Wurster® Air Suspension Coater, or an Aeromatic® Air Suspension Coater can be used for applying the wall or the exterior coat. Other wall and coating techniques such as pan coating can be used for manufacturing the dosage form. In the pan coating system wall forming or coat forming compositions are deposited by successive spraying of the ingredients around the contraceptive steroid accompanied by tumbling in a rotating pan. A pan coater is used to produce a thicker wall or a coat. A larger volume of solvent can be used in a cosolvent system to produce a thinner wall or a coat. Finally, the wall or the coated devices are dried in a forced air oven to free the dosage form of any solvents. Generally, the wall formed by these techniques will have a preferred thickness of 1 to 25 mils (0.03 to 0.64 mm) with a presently preferred thickness of 3 to 10 mils (0.08 to 0.26 mm), and the exterior coat generally will have a thickness of 0.3 to 8 mils (0.008 to 0.20 mm). Of course, thicker walls are encompassed by the invention. Other manufacturing procedures are described in *Modern Plastic*

*Encyclopedia,* Vol. 46, pp 62–70, (1969); and in *Pharmaceutical Sciences,* by Remington, 14th Ed., pp 1626–1978, (1970), published by Mack Publishing Co., Easton, Pa.

The osmotically effective compounds, which are known also as osmagents, as osmotically effective solutes, and as osmotic enhancers, useful for the purpose of this invention, comprise a member selected from the group consisting of water soluble inorganic osmagents and water soluble organic osmagents. The osmagents include a member selected from the group consisting of magnesium sulfate, magnesium chloride, sodium chloride, potassium chloride, lithium sulfate, lithion chloride, potassium sulfate, choline chloride, and the like. The osmotically effective compounds are known in U.S. Pat. Nos. 4,177,256 and 4,449,983.

Exemplary solvent suitable for manufacturing the wall include inert inorganic and organic solvents that do not adversely harm the materials and the final wall. The solvents broadly include a member selected from the group consisting of aqueous solvents selected from the group consisting of aqueous solvents, alcohols, ketones, esters, ethers, aliphatic hydrocarbons, halogenated solvents, cycloaliphatics, aromatics, heterocylic solvents, and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methylpropyl ketone, n-hexane, n-heptane, ethylene glycol monoethyl ether, ethylene glycol monoethyl acetate, methylene dichloride, ethylene dichloride, propylene dichloride, water, acetone and water, acetone and methanol, acetone and ethyl alcohol, methylene dichloride and methanol, ethylene dichloride and methanol, and the like.

DETAILED DISCLOSURE OF EXAMPLES OF THE INVENTION

The following examples are merely illustrative of the present invention and they should not be considered as limiting the scope of the invention in any way, as these examples and other equivalents thereof will become apparent to those versed in the art in the light of the present disclosure, the drawings and the accompanying claims.

EXAMPLE 1

An osmotic dosage form adapted, designed and shaped for delivering contraceptive steroids is manufactured as follows: first, a contraceptive composition is prepared by passing through a 40 mesh screen 456.95 g of polyethylene oxide having a molecular weight of about 100,000. Then, 40 g of polyvinyl pyrrolidone comprising a number average molecular weight of about 38,000, is added to the polyethylene oxide and the two ingredients mixed for about 10 minutes in a conventional mixer. While the two ingredients are mixing, a freshly prepared solution of 0.55 g of ethinyl estradiol dissolved in 250 ml of denatured anhydrous ethanol is slowly added to the mixer and the mixing continued for an additional 10 minutes. The wet granulation is passed through a 20 mesh screen, dried at room temperature for 16 hours and passed again through a 20 mesh screen. Finally, 2.5 g of magnesium stearate is added to the granulation and all the ingredients mixed in a rollermill for 1 to 3 minutes.

The second composition is prepared by mixing 370.0 g of polyethylene oxide having a molecular weight of 4,000,000 with 100 g of sodium chloride and the homogeneous blend passed through a 40 mesh screen. Then, the just prepared polyethylene oxide, sodium chloride blend is mixed with 25.0 g of hydroxypropylmethylcellulose, having a number average molecular weight of 11,200, and with 2.5 g of nontoxic FD & C blue lake #1 for 10 minutes in a mixer. Then, 350 ml of denatured, anhydrous ethanol is added slowly to the blending mixture and all the ingredients mixed for an additional 5 minutes. The freshly prepared wet granulation is passed through a 20 mesh screen, allowed to dry at room temperature for 16 hours, and again passed through a 20 mesh screen. The screened granulation is mixed with 2.5 g of magnesium stearate is a rollermill for 1 minute.

A two-layered press is used for forming the layered arrangement. First, 30 mg of the first composition comprising the contraceptive ethinyl estradiol steroid is added to the press and tamped; then 30 mg of the second layer forming composition is added to the press and the two layers pressed into a contacting layered arrangement.

Next, the layers are surrounded with a semipermeable wall. The wall forming composition comprises 70% cellulose acetate, having an acetyl content of 39.8%, 28% ethylcellulose, and 2% polyethylene glycol having a molecular weight of 3350. The wall forming composition is dissolved in acetone:water (90:10 wt:wt) solvent to make a 4% solids solution. The wall forming composition is sprayed onto and around this bilaminate in an Aeromatic® Air Suspension Coater.

The wall coated bilaminates are dried for 24 hours at room temperature. Then, a 25 mil (0.635 mm) exit orifice is laser drilled on the contraceptive layer side of the osmotic device. The residual solvent is removed by drying the osmotic system for 48 hours at 50° C. and 50% relative humidity. The osmotic systems are then dried for one hour at 50° C. to remove the excess moisture. The osmotic systems are overcoated on the exterior surface on the semipermeable wall. The overcoat comprises 16% norethindrone (0.400 mg) and 0.28% ethinyl estradiol (0.007 mg). The steroid pair are dissolved in a solution comprising 83.72% hydroxypropylcellulose and denatured alcohol to make a 4% solution. The drug overcoat composition is sprayed onto and around the laser drilled delivery system in an Aeromatic® Air Suspension Coater.

Figure 4:
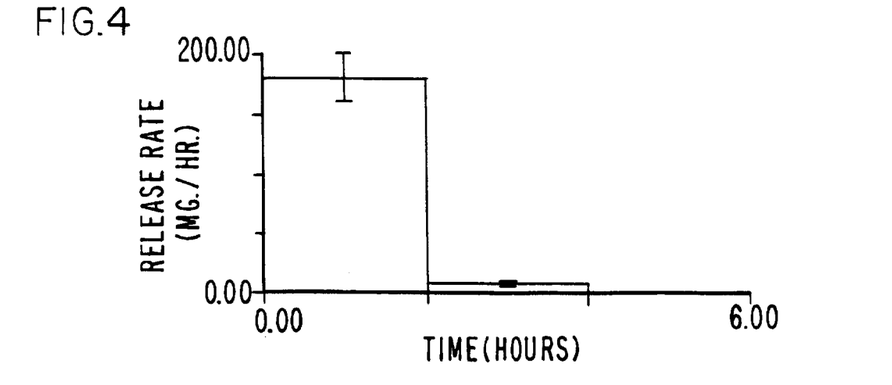
FIG. 4 depicts the release rate of a progestin from an exterior release overcoat on the dosage form.
Figure 5:
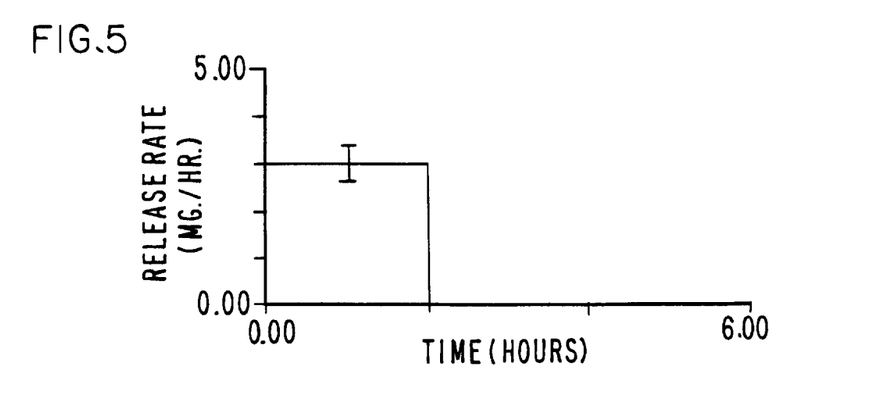
FIG. 5 depicts the quick release of an estrogen from a composition coated onto the exterior surface of the dosage form; and Drawing
Figure 6:
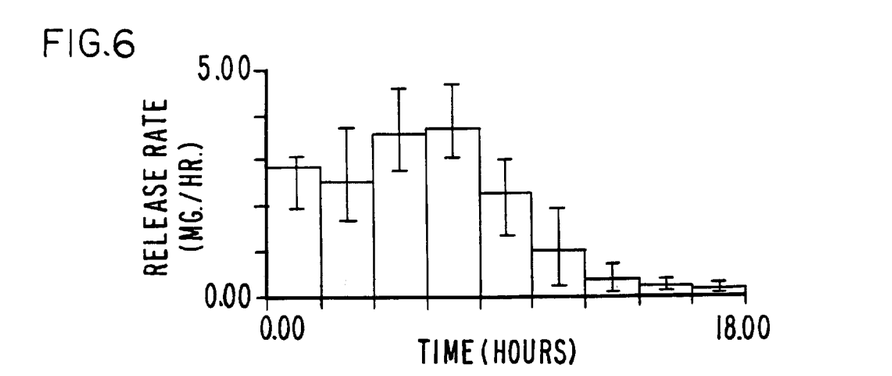
FIG. 6 depicts the release rate of an estrogen from an exterior overcoat and from the internal compartment of a dosage form over a prolonged period up to eighteen hours.

Finally, the osmotic systems are given a color overcoat consisting of commercially available Opadry® blue, a hydroxypropylmethylcellulose, mixed with denatured alcohol:water (90:10 volume:volume) to make a 5% solution. The color composition is sprayed onto and around the drilled delivery system in an Aeromatic® Air Suspension Coater. The residual solvent is removed by drying for 16 hours at 35° C. to yield the operative osmotic dosage forms. Accompanying FIG. 4 depicts the norethindrone release pattern from the exterior overcoat; accompanying FIG. 5 depicts the ethinyl estradiol release pattern from the exterior overcoat; and, accompanying FIG. 6 depicts the release rate per hour for ethinyl estradiol released from the exterior overcoat and the compartment of the dosage form over time.

EXAMPLE 2

The procedure of example 1 is followed in this example, with all conditions as previously described, except for a color overcoat that is made as described in this example. The osmotic system is given a color overcoat to enhance its aesthetic appearance. In one manufacture the osmotic systems are coated with a composition comprising 38.4 g of hydroxypropylmethylcellulose and 4.27 g of polyethylene glycol 3350 to produce a clear overcoat. In another manufacture the osmotic systems are coated with a composition comprising 21.87 g (10% by wt) of hydroxypropylmethylcellulose having a 11.200 molecular weight, 2.46 g (10% by wt) of polyethylene glycol having a 3350 molecular weight and 0.25 g (1.0% by wt) of FD & C blue lake #1 dye to produce a blue overcoat. In an optional manufacture the color overcoat can comprise hydroxypropylmethyl cellulose and diethyl phthalate mixed with denatured alcohol water (90:10 volume:volume) to make a 5% solution. The color composition is sprayed onto and around the drilled delivery system in an Aeromatic® Air Suspension Coater. The residual solvent is removed by drying for 16 hours at 25° C. to yield the operative osmotic dosage form.

EXAMPLE 3

Following the procedure of Example 1, an osmotic dosage form is prepared comprising a first composition which composition comprises 0.033 mg of ethinyl estradiol, 27.417 mg of polyethylene oxide having a 100,000 molecular weight, 2.4 mg of polyvinylpovidone having a molecular weight of 38,000, and 0.15 mg of magnesium stearate; a second composition comprising 22.2 mg of polyethylene oxide having a 6,000,000 molecular weight, 6 mg of sodium chloride, 1–5 mg of a hydroxypropylmethylcellulose having a 11,200 molecular weight, 0.15 mg of blue dye and 0.15 mg of magnesium stearate; a semipermeable wall comprising 6.65 mg of cellulose acetate, having a 43.5 % acetyl content, and 0.35 mg of polyethylene glycol; an orifice diameter of 0.52 mm; and ethinyl estradiol rate of release of 2.158 $\mu$g/hr from the compartment, and an exterior coat comprising 0.28% ethinyl estradiol, 16% norethindrone and 83.72% hydroxypropylcellulose that are released in from zero to 30 minutes when the steroid-coat is contacted by an external fluid.

EXAMPLE 4

The procedure of Example 1 is followed in this example to prepare an osmotic dosage form comprising a first, displaceable composition comprising 0.036 mg of estradiol cypionate, 28.314 mg of polyethylene oxide, having a 200,000 molecular weight, 1–5 mg of polyvinyl pyrrolidone, and 0.15 mg of magnesium stearate; a second composition comprising 22.05 mg of polyethylene oxide, having a 4,000,000 molecular weight, 6.0 mg of sodium chloride 1–5 mg of hydroxypropylmethylcellulose, having a 11,200 molecular weight, 0.30 mg of pharmaceutically acceptable blue dye, and 0.15 mg of magnesium stearate; a wall comprising 5.70 mg of cellulose acetate having a 43.5% acetyl content, and 0.30 mg of polyethylene glycol; an orifice having a diameter of 20 mils (0.52 mm); and a releasable exterior coat comprising estradiol cypionate and levonorgestrel.

EXAMPLE 5

An osmotic dosage form comprising means for the immediate administration of a progestogenic steroid and an estrogenic steroid from an external composition, followed by the twenty-four hour administration of an estrogenic contraceptive, is prepared according to Example 1. In this example a steroid overcoat comprising 3.703 g of norethindrone, 0.065 g of ethinyl estradiol and 38.4 g of hydroxypropylmethylcellulose and 4.27 g of polyethylene glycol are dissolved in denatured, anhydrous ethanol and distilled water (11:2 v:v) and sprayed onto the exterior surface of the semipermeable wall, in an Aeromatic® Air Suspension Coater. Immediately following a sealer coat comprising 21.87 g of hydroxypropylmethylcellulose, 2.46 g of polyethylene glycol and 0.25 g of FD & C blue lake #1 dissolved in denatured anhydrous alcohol and distilled water (90:10 v:v) solvent, to make a 5% solids solution, is sprayed onto the norethindrone ethinyl estradiol overcoat. The osmotic systems are dried for 16 hours at 35° C. to remove residual solvent. The final concentration of the norethindrone in the exterior composition is 0.400 mg, and the final concentration of ethinyl estradiol in the exterior composition is 0.007 mg. The interior compartment contains the single steroid ethinyl estradiol in a concentration of 0.033 mg. The total concentration of ethinyl estradiol comprising the exterior and the interior compartment is 0.04 mg.

EXAMPLE 6

An osmotic dosage form comprising means for immediately administering an estrogenic steroid and a progestogenic steroid from an external composition, followed by prolonged administration of an estrogenic contraceptive steroid, is prepared according to Example 1. In this example, a steroid overcoat comprising 0.065 g of estradiol dipropionate, 3.703 g of norethynodrel and 4.26 g of Opadry, a hydroxypropylcellulose nontoxic carrier, are dissolved in denatured alcohol:water (90:20 v:v) and sprayed on the outer surface of the wall of the osmotic system. Then, a seal coat composition comprising Opadry blue and Opadry clear, (3:1 wt:wt), dissolved in denatured alcohol (90:10 v:v) cosolvent to make a 5% solid solution is sprayed onto the osmotic system comprising estradiol dipropionate in the compartment. The osmotic systems are dried for 16 hours at 35° C. to remove the residual solvent. The final concentration of the steroids in the exterior composition is 0.007 mg of estradiol dipropionate and 0.400 mg of norethynodrel. The Opadry blue composition comprises hydroxypropylmethylcellulose, polyethylene glycol and FD & C blue lake #1. The Opadry clear comprises hydroxypropylmethylcellulose and polyethylene glycol.

EXAMPLE 7

Following the procedure in Example 1, an osmotic device is manufactured comprising an external quick release composition comprising estradiol and norgestrel for delivering 0.005 mg of the ethinyl estradiol and 0.50 mg of the d,l-norgestrel, and internal first composition comprising 0.035 mg of ethinyl estradiol, 84.75 weight percent polyethylene oxide having a 200,000 molecular weight, 10 weight percent hydroxypropylmethylcellulose, having a number average molecular weight of 11,200, and 0.25 weight percent magnesium stearate; an internal second composition comprising 64.75 weight percent polyethylene oxide, having a 7,500,000 molecular weight, 24 weight percent sodium chloride, 10 weight percent hydroxypropylmethylcellulose, having a 11,200 number average molecular weight, 1 weight percent ferric oxide and 0.25 weight percent magnesium stearate; and a semipermeable wall comprising 97 weight percent cellulose acetate having an acetyl content of 39.8% and 3 weight percent polyethylene glycol having a molecular weight of 4000. The device comprises a 20 mil (0.52 mm) exit orifice.

EXAMPLES 8–9

An osmotic dosage form is prepared by following the above described manufacturers. In this example, the external composition comprise 0.008 mg of ethinyl estradiol, 0.50 mg of D-17$\beta$-acetoxy-13$\beta$-ethyl-17$\alpha$-ethinyl-gon-4-en-3-one oxime blended with hydroxypropylcellulose and hydroxypropylmethylcellulose.

An osmotic dosage form is prepared wherein the external composition comprises 1.5 mg of 13$\beta$-ethyl-17$\alpha$-ethinyl- 17β-hydroxygon-4-en-3-one, 0.05 mg of ethinyl estradiol, blended with hydroxypropylcellulose and hydroxypropylethylcellulose.

EXAMPLE 10

A contraceptive dosage form for oral administration to a female recipient desiring contraception is prepared by following the above procedures. In this example the dosage form provided is as follows: a first contraceptive composition weighing 30 mg and comprising 0.11 wt % ethinyl estradiol, 94.39 wt % polyethylene oxide possessing a 100,000 molecular weight, 5 wt % hydroxypropylmethylcellulose possessing a 11,200 molecular weight, and 0.5 mg of magnesium stearate; a second push composition for applying a force against the first composition for pushing it from the dosage form, wherein the second composition weights 30 mg and comprises 74 wt % of a polyethylene glycol possessing a 7,500,000 molecular weight, 20 wt % of sodium chloride, 5 wt % of hydroxypropylmethylcellulose possessing a 11,200 molecular weight, 0.5 wt % of FD & C blue like #1 dye, and 0.5 wt % of magnesium stearate. The dosage form comprises a semipermeable wall weighing 7.00 mg, which wall comprises 95 wt % of a cellulose acetate comprising a 43.5% acetyl content and 5 wt % of polyethylene glycol possessing a 3350 molecular weight. An instant steroid release overcoat is in contact with the exterior surface of the semipermeable wall, which instant overcoat comprises 0.70 wt % ethinyl estradiol, 1.47 wt % norethindrone, 90 wt % hydroxypropylmethylcellulose possessing a 11,200 molecular weight and 9.30 wt % of polyethylene glycol possessing a 3350 molecular weight. In an optional embodiment a second steroid-free overcoat on the outermost surface of the dosage form weighs 2.00 mg and comprises 90 wt % hydroxypropylmethylcellulose possessing a 11,200 molecular weight and 10 wt % of polyethylene glycol possessing a 3350 molecular weight. The dosage form as an 0.52 mm exit passageway.

EXAMPLE 11

Following the procedure of Example 1, an osmotic dosage form is prepared comprising a first composition consisting essentially of 0.039 mg of ethinyl estradiol, 28.31 mg of polyethylene oxide having a 100,000 molecular weight, 1.5 mg of hydroxypropylmethylcellulose a 11,200 molecular weight, and 0.15 mg of magnesium stearate; a second composition comprising 22.2 mg of polyethylene oxide having a 6,000,000 molecular weight, 6 mg of sodium chloride, 1.5 mg of a hydroxypropylmethylcellulose having a 11,200 molecular weight, 0.15 mg of blue dye and 0.15 mg of magnesium stearate; a wall comprising 6.65 mg of cellulose acetate, having a 43.5% acetyl content, and 0.35 mg of polyethylene glycol; an orifice diameter of 2.0 mils (0.52 mm), and an ethinyl estradiol rate of release of 2.158 μg/hr, and an exterior aqueous releasable coat comprising 0.0825 mg of norethindrone and 0.008 mg of ethinyl estradiol.

EXAMPLE 12

A dosage form is prepared according to the procedures of this example for providing a dosage form comprising a first composition comprising maltrodertrin, hydroxypropylcellulose and an estrogenic steroid, and a second composition comprising sodium carboxymethyl cellulose.

DISCLOSURE OF A METHOD OF USING THE INVENTION

An embodiment of the invention pertains to a method for delivering beneficial contraceptive steroids orally in an instant dose and at a rate controlled dose to a female recipient in need of contraception. The method comprises the steps of: (A) admitting into the female an osmotic dosage form comprising: (1) a wall surrounding a compartment, the wall comprising at least in part a semipermeable polymer composition permeable to the passage of fluid and substantially impermeable to the passage of contraceptive steroid; (2) a composition comprising a contraceptive estrogen steroid and a contraceptive progestogen steroid on the exterior surface of the wall of dosage form; (3) a composition comprising an estrogenic steroid in the compartment in an amount for performing a contraceptive program; (4) a layer in the compartment comprising a composition for imbibing and absorbing fluid for pushing the composition comprising the estrogenic steroid from the osmotic dosage form; and (5) at least one passageway in the wall for connecting the exterior of the dosage form with the interior compartment of the dosage form; (B) releasing the estrogen and progestogen from the exterior coat by contacting the coat with a biological fluid for providing immediate fertility control; (C) imbibing fluid through the semipermeable part of the wall at a rate determined by the permeability of the semipermeable wall and the osmotic pressure gradient across the semipermeable wall thereby causing the osmotic layer to expand and swell; and (D) delivering the contraceptive estrogen steroids from the compartment of the dosage form through the exit passageway to the recipient for fertility control, and wherein the dosage form is administered orally for 18 to 23 days to provide an estrogenic activity equivalent to 0.002 mg to 1.000 mg of ethinyl estradiol and a progestogenic activity equivalent to 0.005 mg to 250 mg of a progestational steroid selected from the group consisting of progesterone, d-norgestrel, norethindrone, also known as 19-norethisterone, levonorgestrel, norgestimate, norgestrel, norethindrone acetate, also known as norethisterone acetate, norethynodrel, norethindrone acetate, 17-hydroxyprogesterone, 17-hydroxyprogesterone ester, 19-nor-17-hydroxyprogesterone, 19-nor-17-hydrogesterone ester, 17α-ethinyl testosterone, 17α-ethinyl-19-nortestosterone. D-17β-acetoxy-13β-ethyl-17α-ethinyl-gon-4-en-3-one oxime, d-13β-ethyl-17α-ethinyl-17β-hydroxygon-4-en-3-one, 13β-ethyl-17β-hydroxygon-4-en-3-one, 13β,17α-diethyl-17β-hydroxygon-4-en-3-one, medroxyprogesterone acetate, ethylnodiol diacetate, medroxyprogesterone, chlormadrone acetate, dimethistrone, 17α-ethinyl-17β-acetoxy-19-norandrost-4-en-3-one oxime, 3-keto desogestrel, desogestrel, gestodene, medroxyprogesterone, medroxyprogesterone acetate and megestrol acetate, and, medroxyprogesterone acetate and megestrol.

While the invention has been described and pointed out in detail, as applied to preferred embodiments, those skilled in the art will appreciate that various modifications, changes and omissions in the delivery system and the delivery program described herein can be made without departing from the spirit of the invention.

We claim:

1. A method for providing contraception to a woman of childbearing age, wherein the method comprises: administering orally to the woman a dosage form comprising an internal composition comprising a pharmaceutically-acceptable estrogenically-active contraception-regulating steroid, and an overcoat comprising a pharmaceutically-acceptable progestationally-active contraception-regulating steroid, and wherein the method is characterized by the dosage form delivering orally the estrogenically-active steroid in a controlled dose of 0.2 micrograms to 30 micrograms per hour over an extended period up to 24 hours for contraceptive control, compared to a dosage form that delivers an estrogenically-active steroid in an uncontrolled dose, and the progestationally-active steroid is delivered in a dose of 10 nanograms to 150 milligrams in an instantly released dose of from zero to sixty minutes from the dosage form overcoat to provide contraception.

2. A method for providing contraception to a woman of childbearing age, wherein the method comprises: administering orally to the woman a dosage from comprising an overcoat comprising 10 nanograms to 25 milligrams of a pharmaceutically acceptable estrogenically-active contraception-regulating steroid and 15 nanograms to 150 milligrams of a pharmaceutically-acceptable progestationally-active contraception-regulating steroid that are delivered in an instantly released dose of from zero to sixty minutes from the dosage form overcoat to provide contraception.

* * * * *